(12) United States Patent
Deshays

(10) Patent No.: US 8,334,521 B2
(45) Date of Patent: Dec. 18, 2012

(54) MEDICAL INSTRUMENT DISINFECTING SYSTEM

(75) Inventor: Clement Deshays, Ruoms (FR)

(73) Assignee: Germitec, Clichy (FR)

( * ) Notice: Subject to any disclaimer, the term of this patent is extended or adjusted under 35 U.S.C. 154(b) by 721 days.

(21) Appl. No.: 12/066,872

(22) PCT Filed: Dec. 5, 2005

(86) PCT No.: PCT/FR2005/003032
§ 371 (c)(1),
(2), (4) Date: Mar. 14, 2008

(87) PCT Pub. No.: WO2007/031613
PCT Pub. Date: Mar. 22, 2007

(65) Prior Publication Data
US 2008/0219899 A1 Sep. 11, 2008

(30) Foreign Application Priority Data
Sep. 15, 2005 (FR) ...................................... 05 09452

(51) Int. Cl.
*G01N 23/00* (2006.01)
*H01J 37/20* (2006.01)
(52) U.S. Cl. ................. 250/455.11; 340/10.1; 340/10.4; 340/10.41; 340/505; 340/539.1; 340/571.1; 340/568.1; 340/572.8; 340/572.1; 422/186.3; 422/292; 422/300; 422/33; 422/58; 422/51
(58) Field of Classification Search ............. 250/455.11; 340/10.1, 10.4, 10.41, 505, 539.1, 571.1, 340/568.1, 572.8, 572.1; 422/186.3, 292, 422/300, 33, 58, 51
See application file for complete search history.

(56) References Cited

U.S. PATENT DOCUMENTS

| 4,772,795 A | 9/1988 | Sakurai et al. |
| 5,185,532 A | 2/1993 | Zabsky et al. |
| 5,310,524 A | 5/1994 | Campbell et al. |
| 5,610,811 A | 3/1997 | Honda |

(Continued)

FOREIGN PATENT DOCUMENTS

DE 3209701 A1 9/1983

(Continued)

OTHER PUBLICATIONS

International Search Report mailed on Jan. 22, 2009, for PCT Application No. PCT/FR2008/000541, 3 pages.

(Continued)

*Primary Examiner* — Jack Berman
*Assistant Examiner* — Meenakshi Sahu
(74) *Attorney, Agent, or Firm* — Morrison & Foerster LLP

(57) ABSTRACT

The invention concerns a medical instrument disinfecting system (1) comprising a disinfecting chamber (4) adapted to implement a cycle for disinfecting the instruments. The invention is characterized in that each instrument (1) comprises identification data (5) and in that the chamber (4) is associated with means (6) for acquiring the identification data of the or each instrument (1) when it is introduced into or withdrawn from the chamber (4) at the start and at the end of a disinfecting cycle, with means (7, 8) for acquiring characterization data of the disinfecting cycle and with means (9, 10, 11, 12, 13) for associating the identification data of the or each instrument and the characterization data of the disinfecting cycle to generate traceability data of the disinfection of the or each instrument.

25 Claims, 1 Drawing Sheet

U.S. PATENT DOCUMENTS

| | | | |
|---|---|---|---|
| 5,641,464 A | 6/1997 | Briggs, III et al. | |
| 5,690,113 A | 11/1997 | Sliwa, Jr. et al. | |
| 5,761,069 A * | 6/1998 | Weber et al. | 700/213 |
| 6,039,928 A | 3/2000 | Roberts | |
| 6,171,559 B1 | 1/2001 | Sanders et al. | |
| 6,231,819 B1 * | 5/2001 | Morello | 422/186.3 |
| 6,260,560 B1 | 7/2001 | Walta | |
| 6,475,433 B2 * | 11/2002 | McGeorge et al. | 422/24 |
| 6,485,979 B1 * | 11/2002 | Kippenhan et al. | 436/1 |
| 6,641,781 B2 | 11/2003 | Walta | |
| 7,965,185 B2 | 6/2011 | Cambre et al. | |
| 2001/0024623 A1 | 9/2001 | Grimm et al. | |
| 2002/0162972 A1 | 11/2002 | Pleet | |
| 2003/0016122 A1 | 1/2003 | Petrick | |
| 2003/0039579 A1 | 2/2003 | Lambert et al. | |
| 2003/0187586 A1 | 10/2003 | Katzenmaier et al. | |
| 2004/0009091 A1 | 1/2004 | Deal et al. | |
| 2004/0140347 A1 | 7/2004 | Mihaylov et al. | |
| 2004/0209223 A1 | 10/2004 | Beier et al. | |
| 2005/0196314 A1 | 9/2005 | Petersen et al. | |
| 2008/0213139 A1 | 9/2008 | Deshays | |
| 2008/0219899 A1 | 9/2008 | Deshays | |
| 2009/0169436 A1 | 7/2009 | Deshays | |
| 2010/0140134 A1 | 6/2010 | Deshays | |
| 2010/0140342 A1 | 6/2010 | Deshays | |

FOREIGN PATENT DOCUMENTS

| | | |
|---|---|---|
| DE | 3917876 A1 | 12/1990 |
| DE | 19703823 C1 | 5/1998 |
| DE | 19917206 A1 | 10/2000 |
| DE | 10225232 A1 | 12/2002 |
| DE | 10225857 A1 | 1/2004 |
| EP | 0 471 530 A | 2/1992 |
| EP | 0 630 820 A | 12/1994 |
| EP | 0 709 056 A1 | 5/1996 |
| EP | 0 709 056 B1 | 5/1996 |
| EP | 0839537 A1 | 5/1998 |
| EP | 1 402 904 A | 3/2004 |
| EP | 1 532 989 A1 | 5/2005 |
| FR | 2753905 | 4/1998 |
| FR | 2890566 A1 | 3/2007 |
| FR | 2890865 A1 | 3/2007 |
| WO | WO-84/00009 A1 | 1/1984 |
| WO | WO-99/08137 A1 | 2/1999 |
| WO | 2004/111917 A1 | 12/2004 |
| WO | WO-2005/048041 A2 | 5/2005 |
| WO | WO-2005/048041 A3 | 5/2005 |

OTHER PUBLICATIONS

International Search Report mailed on Sep. 11, 2007, for PCT Application No. PCT/FR2007/000594, 3 pages.

International Search Report mailed on Mar. 21, 2006 for PCT Application No. PCT/FR2005/003031, 3 pages.

International Search Report of PCT/FR2005/003032, date of mailing Jul. 6, 2006.

International Search Report of PCT/FR2005/000594, date of mailing Sep. 11, 2007, ISR of co-pending U.S. Appl. No. 12/296,571.

* cited by examiner

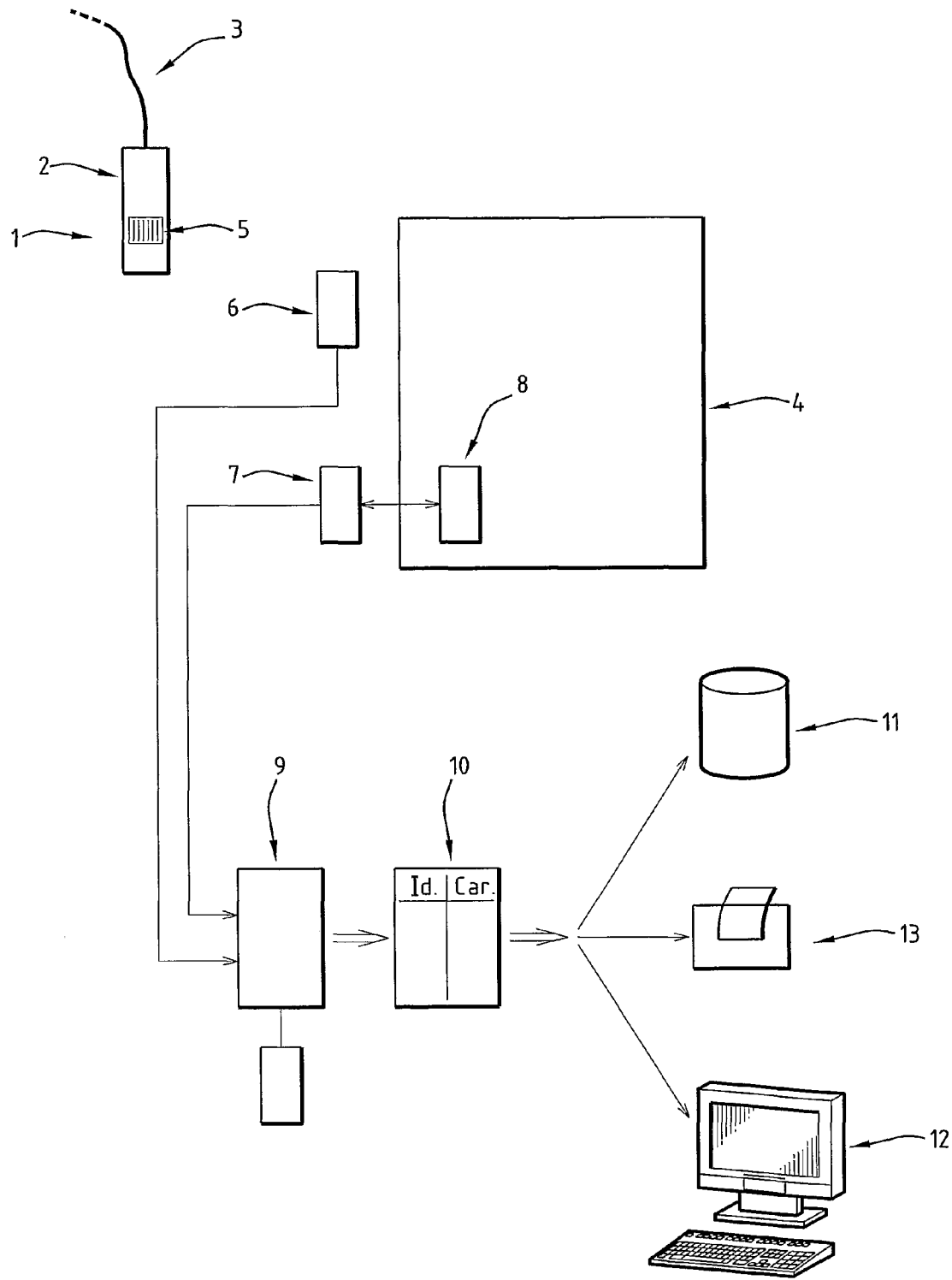

MEDICAL INSTRUMENT DISINFECTING SYSTEM

The present invention concerns a medical instrument disinfecting system.

Disinfecting systems of this type are already known in the art, which comprise, for example, a disinfecting chamber adapted to perform an instrument disinfecting cycle.

These chambers can be, for example, chambers associated with means for emitting a UV radiation, for example, of the UVC type, or with chemical disinfecting means, etc.

By way of example, reference can be made to the document EP-A-0839537, which describes an instrument supporting device in a chamber, in particular a decontamination chamber, and a corresponding chamber.

Actually, this document concerns a medical instrument decontamination chamber delimited by a bottom, at least one lateral wall, and an upper lid, each instrument having an active portion and a connecting portion in the form of a cable.

This chamber also has a boom extending within and at the upper part of the chamber, parallel to the bottom and overhanging the bottom, this boom comprising a plurality of suspending members, each of which is intended to cooperate with a portion of the cable neighboring the active portion of the instrument.

This chamber is also associated with means, for example, using tubes, for emitting in the chamber UV radiation, for example, C type UV radiation, for example, to ensure the disinfection of the instruments.

Of course, other disinfection means can be envisioned.

However, all these systems of the state of the art have a number of problems, in particular regarding the traceability of the instrument disinfection.

The objective of the invention is thus to remedy these problems.

To this effect, an object of the invention is a disinfecting chamber adapted to implement an instrument disinfecting cycle, characterized in that each instrument has identification data and in that the chamber is associated with means for acquiring identification data of the or each instrument when it is put in place and when it is removed from the chamber at the start and at the end of a disinfecting cycle, with means for acquiring characterization data of the disinfecting cycle, and with means for associating the identification data of the or each instrument and the characterization data of the disinfecting cycle to generate traceability and disinfection data of the or each instrument.

According to particular embodiments, the chamber according to the invention can comprise one or several of the following characteristics:
- the identification data of each instrument are in the form of a bar code and the corresponding acquisition means of the chamber comprise a code reader;
- the chamber has a boom for suspending the instruments and the reader is fixed to this boom;
- the means for acquiring characterization data of the disinfecting cycle comprise means for acquiring data selected from the data group including identification data of the chamber and time-stamping data of the disinfecting cycle;
- the chamber has means for generating an UV radiation for disinfecting the instruments and the characterization data of the disinfecting cycle comprise data on the UV dose emitted during the cycle, provided by a corresponding sensor implanted in the chamber;
- the UV sensor is implanted under the boom of the chamber;
- the means for associating the data are associated with means for displaying this data, for storing this data, and/or for printing this data;
- the means for associating the data are adapted to emit traceability data only if the corresponding instrument has actually been identified when it is put in place and when it is removed from the chamber before and after the disinfecting cycle, respectively.

The invention will be better understood from the following description, which is given by way of example only, with reference to the annexed drawing which represents a schematic synoptic view illustrating the structure and operation of a disinfecting system according to the invention.

Thus, on this FIGURE, a medical instrument disinfecting system has been illustrated.

Such an instrument is, for example, designated by the general reference numeral 1 on this FIGURE and is in the form of a sensor, of the sonogram sensor type or other.

Then, this sensor has an active portion designated by the general reference numeral 2 and a connecting cable designated by the general reference numeral 3.

This sensor is adapted to be put in place and removed from a disinfecting chamber designated by the general reference numeral 4 on the FIGURE. This disinfecting chamber is adapted to implement a disinfecting cycle of the instruments.

As has been mentioned above, various types of chambers and various types of disinfecting cycles can be envisioned, for example, by radiation, chemical, or other.

In the system according to the invention, each instrument has identification data of this instrument.

By way of example, this identification data can be constituted by a bar code designated by the general reference numeral 5 on the FIGURE, this bar code being carried, for example, by the active portion, or by the connecting cable of the instrument.

Of course, other embodiments can be envisioned.

Then, the chamber is associated with means for acquiring this identification data of each instrument.

These means for acquiring this identification data are designated by the general reference numeral 6 on this FIGURE and they comprise, for example, any appropriate sensor such as, for example, a code bar reader or other.

Then, this sensor is adapted to acquire the identification data of the or each instrument when it is put in place and when it is removed from the chamber at the start and at the end of a disinfecting cycle.

By way of example, these acquisition means can be in the form of a sensor external to the chamber, which is, for example, in the form of a "scanhead" type sensor or in the form of a sensor directly integrated into the disinfecting chamber, for example, on the boom of the chamber described in the above-mentioned document EP-A-0839537.

In addition, the chamber is associated with means for acquiring characterization data of the decontamination cycle, i.e., more particularly the conditions of its performance.

These means are designated by the general reference numeral 7 on this FIGURE and they can include various types of data acquisition means adapted to acquire data selected from the data group comprising, for example, identification data of the chamber, each chamber being then equipped with a specific identification number stored in this chamber, time-stamping data of the cycle making it possible, for example, to acquire the date of the cycle, the number of the cycle in the day, the time at the start and the time at the end of the cycle, from a clock-forming circuit, etc.

This characterization data can also include data regarding the UV dose emitted during a cycle, if the chamber is a disinfecting chamber equipped with means for generating disinfecting UV radiation.

This data can then be determined from a sensor of any appropriate type already known in the art and designated, for example, by the general reference numeral 8 on this FIGURE.

This sensor can be put in place, for example, under the boom of the chamber described in the above-mentioned EP document.

These various data, i.e., the identification data of the or each instrument and the characterization data of the disinfecting cycle, are then transmitted to an data processing unit designated by the general reference numeral 9 on this FIGURE and constituted by any appropriate computer, for example, integrated into the means for controlling the operation of the chamber, to implement a function associating this data in order to generate traceability data and on disinfection.

Thus, this data processing unit 9 is adapted to associate the identification data of the or each instrument present in the chamber during a disinfecting cycle with the characterization data of the performance of the cycle, in order to supply data on the performance of this cycle, in order to supply data making it possible to ensure the traceability of the disinfection of the or each instrument.

This traceability data is designated by the general reference numeral 10 on the FIGURE and it makes it possible to relate each instrument to the conditions in which the corresponding disinfecting cycle was performed.

It is to be noted that this traceability data can be emitted only if an instrument has actually been identified when it is introduced in the chamber before the start of the cycle and when it is removed from the chamber after the end of this cycle.

Thus, the operator must necessarily identify the instrument when it is put in place and when it is removed from the chamber. Otherwise, the data processing unit does not generate the traceability data.

This traceability data is then available to ensure the traceability of the disinfection operation, so as, for example, to store this data in data storage means as illustrated at 11 on this FIGURE, to visualize this data, for example, on a display device of any type, designated by the general reference numeral 12, or to print this data, for example, using a printing means of any type, such as a printer designated by the general reference numeral 13.

It will be noted, for example, that such a printer can be adapted to print the traceability data on a sticker that can be associated, for example, to a file of the patient that was in contact with the disinfected instrument, a traceability register, etc.

By way of example, the characterization data carried by this sticker can then include data on the UV dose received by the instrument during its passage in the disinfecting chamber, this dose being determined, for example, from the power or UV illumination emitted during the cycle multiplied by the duration of this cycle.

That is, it is known that this parameter can be crucial in order to obtain a given level of disinfection of the instruments.

It is then understood that such a system makes it possible to ensure an optimal traceability of the disinfection of instruments of this type, in-so-far the traceability data makes it possible to guarantee the passage of the instrument in the chamber and to verify the characterization data of the disinfecting cycle to which the instrument was subjected, i.e., in particular, the moment when this disinfection took place, the chamber in which the disinfecting cycle was performed, and the dose, in particular UV dose, received by the instrument.

Of course, other embodiments can be envisioned.

The invention claimed is:

1. Medical instrument disinfecting system comprising:
    a disinfecting chamber adapted to implement an instrument disinfection cycle of an instrument, wherein the instrument has an active part and a cable connection and respective identification data identifying said instrument carried on the cable connection,
    means for acquiring the respective identification data of the instrument subjected to the disinfection cycle (i) at a first time during a first time period from an introduction of said instrument into the chamber to a start of the disinfection cycle, and (ii) at a second time during a second time period from an end of the disinfection cycle to a removal of said instrument from the chamber,
    wherein the identification data acquiring means is associated with the disinfecting chamber,
    means for acquiring characterization data of the disinfection cycle, and
    means for associating the identification data of each instrument subjected to the disinfection cycle and the characterization data of the disinfecting cycle,
    so as to generate traceability data of the disinfection of the instrument subjected to the disinfection cycle in the disinfection chamber.

2. Disinfecting system according to claim 1, wherein the identification data of the instrument is in the form of a bar code and the corresponding acquisition means of the chamber comprise a code reader.

3. Disinfecting system according to claim 2, wherein the chamber has a boom for suspending the instruments and the reader is fixed to this boom.

4. Disinfecting system according to claim 1, wherein the means for acquiring characterization data of the disinfecting cycle comprise means for acquiring data selected from the data group comprising identification data of the chamber and time-stamping data of the disinfecting cycle.

5. Disinfecting system according to claim 1, wherein the chamber includes means for generating an UV radiation for disinfection of the instrument and the characterization data of the disinfecting cycle comprise data on the UV dose emitted during the cycle, supplied by a corresponding sensor implanted in the chamber.

6. Disinfecting system according to claim 5, wherein the chamber has a boom for suspending the instruments and the reader is fixed to this boom, and wherein the UV sensor is implanted under the boom of the chamber.

7. Disinfecting system according to claim 1, wherein the means for associating the data are associated with means for displaying this data, for storing this data, and/or for printing this data.

8. Disinfecting system according to claim 1, wherein the means for associating the data are adapted to emit traceability data only if the corresponding instrument has actually been identified when it is put in place and when it is removed from the chamber before and after the disinfecting cycle, respectively.

9. Disinfecting system according to claim 2, wherein the means for acquiring characterization data of the disinfecting cycle comprise means for acquiring data selected from the data group comprising identification data of the chamber and time-stamping data of the disinfecting cycle.

10. Disinfecting system according to claim 3, wherein the means for acquiring characterization data of the disinfecting cycle comprise means for acquiring data selected from the data group comprising identification data of the chamber and time-stamping data of the disinfecting cycle.

11. Disinfecting system according to claim 2, wherein the chamber includes means for generating an UV radiation for disinfection of the instrument and the characterization data of the disinfecting cycle comprise data on the UV dose emitted during the cycle, supplied by a corresponding sensor implanted in the chamber.

12. Disinfecting system according to claim 3, wherein the chamber includes means for generating an UV radiation for disinfection of the instrument and the characterization data of the disinfecting cycle comprise data on the UV dose emitted during the cycle, supplied by a corresponding sensor implanted in the chamber.

13. Disinfecting system according to claim 4, wherein the chamber includes means for generating an UV radiation for disinfection of the instrument and the characterization data of the disinfecting cycle comprise data on the UV dose emitted during the cycle, supplied by a corresponding sensor implanted in the chamber.

14. Disinfecting system according to claim 9, wherein the chamber includes means for generating an UV radiation for disinfection of the instrument and the characterization data of the disinfecting cycle comprise data on the UV dose emitted during the cycle, supplied by a corresponding sensor implanted in the chamber.

15. Disinfecting system according to claim 10, wherein the chamber includes means for generating an UV radiation for disinfection of the instrument and the characterization data of the disinfecting cycle comprise data on the UV dose emitted during the cycle, supplied by a corresponding sensor implanted in the chamber.

16. Disinfecting system according to claim 11, wherein the chamber has a boom for suspending the instruments and the reader is fixed to this boom, and wherein the UV sensor is implanted under the boom of the chamber.

17. Disinfecting system according to claim 12, wherein the chamber has a boom for suspending the instrument and the reader is fixed to this boom, and wherein the UV sensor is implanted under the boom of the chamber.

18. Disinfecting system according to claim 13, wherein the chamber has a boom for suspending the instrument and the reader is fixed to this boom, and wherein the UV sensor is implanted under the boom of the chamber.

19. Disinfecting system according to claim 14, wherein the chamber has a boom for suspending the instrument and the reader is fixed to this boom, and wherein the UV sensor is implanted under the boom of the chamber.

20. Disinfecting system according to claim 15, wherein the chamber has a boom for suspending the instrument and the reader is fixed to this boom, and wherein the UV sensor is implanted under the boom of the chamber.

21. Disinfecting system according to claim 1, wherein the acquisition means is in the form of a sensor directly integrated into the disinfecting chamber.

22. Disinfecting system according to claim 21, wherein the chamber has a boom for suspending the instrument and the sensor is fixed to this boom.

23. Method for disinfecting medical instruments in a disinfecting chamber adapted to implement an instrument disinfection cycle of an instrument, wherein the instrument has an active part and a cable connection and respective identification data identifying said instrument carried on the cable connection, said method comprising:
  acquiring the respective identification data of the instrument subjected to the disinfection cycle (i) at a first time during a first time period from an introduction of said instrument into the chamber to a start of the disinfection cycle, and (ii) at a second time during a second time period from an end of the disinfection cycle to a removal of said instrument from the chamber,
  wherein the identification data acquiring means is associated with the disinfecting chamber,
  acquiring characterization data of the disinfection cycle, and
  associating the respective identification data of the instrument subjected to the disinfection cycle and the characterization data of the disinfecting cycle,
  so as to generate traceability data of the disinfection of the instrument subjected to the disinfection cycle in the disinfection chamber.

24. Disinfecting method according to claim 23, wherein the identification data is acquired using a sensor directly integrated into the disinfecting chamber.

25. Disinfecting method according to claim 24, wherein the chamber has a boom for suspending the instruments and the sensor is fixed to this boom.

\* \* \* \* \*